US00PP19511P2

(12) United States Plant Patent
Navero et al.

(10) Patent No.: US PP19,511 P2
(45) Date of Patent: Dec. 2, 2008

(54) OLIVE TREE NAMED 'CHIQUITITA'

(50) Latin Name: ***Olea europaeal*/Olive Tree**
Varietal Denomination: Chiquitita

(75) Inventors: Diego Barranco Navero, Córdoba (ES); Luis Rallo Romero, Córdoba (ES)

(73) Assignee: Universidad de Córdoba, Córdoba (ES)

( * ) Notice: Subject to any disclaimer, the term of this patent is extended or adjusted under 35 U.S.C. 154(b) by 0 days.

(21) Appl. No.: 11/806,947

(22) Filed: Jun. 5, 2007

(51) Int. Cl.
*A01H 5/00* (2006.01)

(52) U.S. Cl. ..... Plt./158

(58) Field of Classification Search ..... Plt./158
See application file for complete search history.

*Primary Examiner*—Annette H Para
(74) *Attorney, Agent, or Firm*—Buchanan Ingersoll & Rooney PC

(57) ABSTRACT

A new and distinct *Olea europaea* cultivar is provided that forms attractive black olives having a high oil content. The fruit weight is greater than that of the 'Arbequina' cultivar (non-patented in the United States). The tree possesses low vigor and displays a compact and weeping growth habit that is well adapted for growing in high density orchards. The tree also displays an ability to form an olive crop at an early age.

3 Drawing Sheets

Botanical/commercial classification: *Olea europaea*/Olive Tree.
Varietal denomination: cv. Chiquitita.

BACKGROUND OF THE NEW CULTIVAR

The new cultivar of *Olea europaea* was created by artificial pollination during the course of a breeding program wherein two parents were crossed which previously had been studied in the hope that they would contribute the desired characteristics. Such breeding program was a cooperative program conducted by the University of Córdoba and the Andalusian Agriculture Research and Training Institute (IFAPA) at Córdoba, Spain.

The parental cultivars were of different geographical origin with each having high productivity and oil content. The female parent (i.e., the seed parent) was the 'Picual' cultivar (non-patented in the United States) from Andalusia in southern Spain. The male parent (i.e. the pollen parent) was the 'Arbequina' cultivar (non-patented in the United States) from Catalonia in northeastern Spain.

The parentage of the new cultivar can be summarized as follows:

'Picual'×'Arbequina'.

The original seedling of the cross carried out in 1991 initially was designated UC-I 8-7 in breeding records. This seedling was planted in the field during 1994 at the experimental farm of IFAPA Centro Alameda del Obispo of Córdoba, Spain. The first olive crop was produced during 1996 and the resulting plant was evaluated during the succeeding harvest seasons.

It was found that the new olive cultivar of the present invention possesses the following combination of characteristics:

(a) displays low vigor and a compact and weeping growth habit that is adapted for growing in high density orchards, (b) displays an ability to form an olive crop at an early age, and (c) efficiently forms attractive olives having a high oil content.

The new cultivar can be distinguished from its parental cultivars and all other olive cultivars known to the orginiators.

The new cultivar is particularly well suited for growing as an alternative cultivar in high density hedgerow orchards where the male parent 'Arbequina' cultivar has been utilized as a standard cultivar in the past. The new cultivar in view of its reduced vigor is believed to be a superior candidate for ease of management in a high density hedgerow orchard system. Hereafter the characteristics of the new cultivar are compared in detail with those of the 'Arbequina' cultivar.

The new cultivar has been found to undergo asexual propagation beginning in February 2000 at Córdoba, Spain, by the use of semi-hardwood stem cuttings. Propagated trees of the new cultivar were planted for further evaluation at the experimental farm of IFAPA Centro Alameda del Obispo of Córdoba, Spain, together with fourteen other previously known genotypes which were used as controls. A randomized block design with sixteen replications and one tree per elementary plot was utilized. The evaluation of this trial confirmed prior results that were observed during the seedling stage. Accordingly, the new cultivar has been found to undergo asexual propagation in a true to type manner.

The new cultivar has been named 'Chiquitita'.

BRIEF DESCRIPTION OF THE PHOTOGRAPHS

The accompanying photographs show as nearly true as it is reasonably possible to make in color illustrations of this character typical specimens of the new variety. The plants was being grown during November 2006 at Córdoba, Spain.

DETAILED DESCRIPTION

Figure 1:
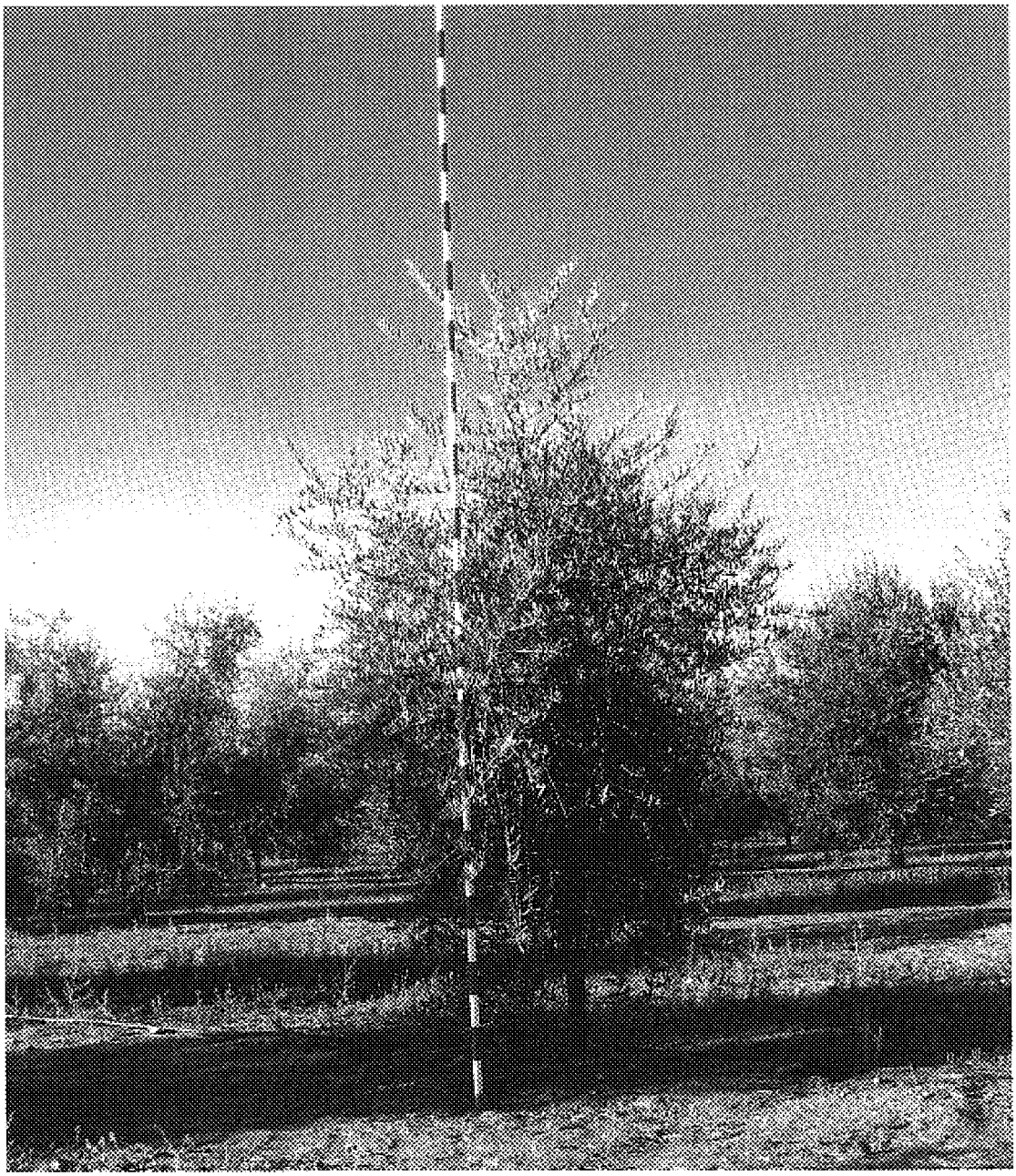
FIG. 1 illustrates a typical tree at the age of approximately six years. The tree height is approximately 2.2 to 2.5 meters and the compact and weeping growth habit is illustrated.

The following description is based upon the observation of the original tree of the new cultivar as well as upon the observation of propagated trees growing at the experimental farm of IFAPA Centro Alameda del Obispo previously identified. The chart used in the identification of the colors is that of The Royal Horticultural Society (R.H.S. Colour Chart), London, England.

Classification: *Olea europaea* L.

Tree:

*Vigor.*—Weak, and significantly lower than that of the 'Arbequina' cultivar which commonly is considered to display low to medium vigor.

*Height.*—Less than that of the 'Arbequina' cultivar at a given age, and commonly under 3 m five years after planting.

*Width.*—Less than that of the 'Arbequina' cultivar at a given age, and commonly under 2 m five years after planting.

*Trunk.*—The diameter 1 m above the ground commonly is approximately 2.2 cm at two years of age, approximately 5.6 cm at four years of age, and approximately 8.6 cm at six years of age.

*Bark.*—Commonly Greyed-Green Group 197C in coloration, generally smooth in texture, and similar to that of the 'Arbequina' cultivar.

*Branches.*—Generally smooth in texture, approximately 4 cm in diameter at an age of six years, and commonly Yellow-Green Group 147B in coloration.

*Lenticels on branches.*—Elongated, small with approximately 8 being present over an area of 1 $cm^2$, and commonly Greyed-Orange Group 165D in coloration.

*Growth habit.*—Somewhat drooping and weeping when bearing a crop which can be compared to the more spreading growth character of the 'Arbequina' cultivar.

*Canopy density.*—Dense and compact.

*Canopy volume.*—Three years after planting approximately 2.7±0.4 $m^3$ on average compared to 4.1±0.5 $m^3$ on average for the 'Arbequina' cultivar; four years after planting approximately 3.9±0.6 $m^3$ on average compared to approximately 5.2±0.6 on average for the 'Arbequina' cultivar; and approximately 5 years after planting approximately 5.5±0.7 $m^3$ on average compared to 7.4±0.8 $m^3$ for the 'Arbequina' cultivar.

*Juvenile period.*—Short, during observations to date slightly shorter than that of the 'Arbequina' cultivar, three years after planting all trees commonly bear fruit, and the average unproductive period was observed to be 2.1 years for the new cultivar and 2.5 years for the 'Arbequina' cultivar.

Foliage:

*Configuration.*—Elliptic-lanceolate.

*Length.*—Relatively short, commonly approximately 50 mm on average.

*Width.*—Relatively narrow, commonly approximately 11 mm at the widest point.

Figure 2:
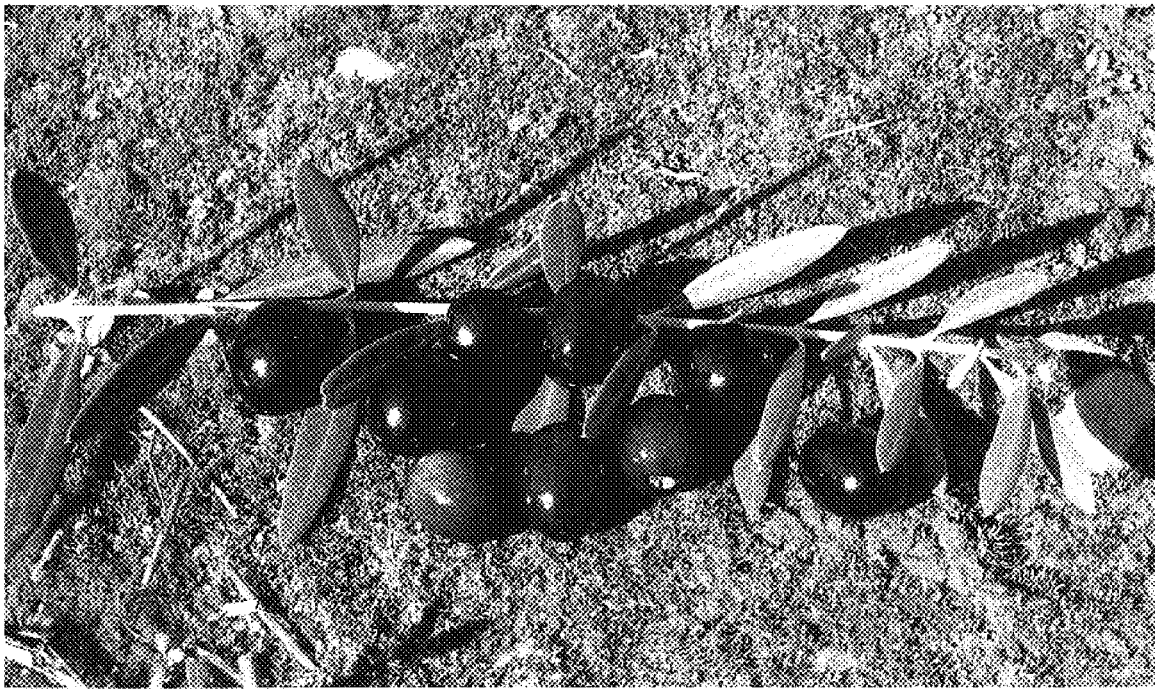
FIG. 2 illustrates typical fruit in various stages of ripening and foliage of the new cultivar.
Figure 3:
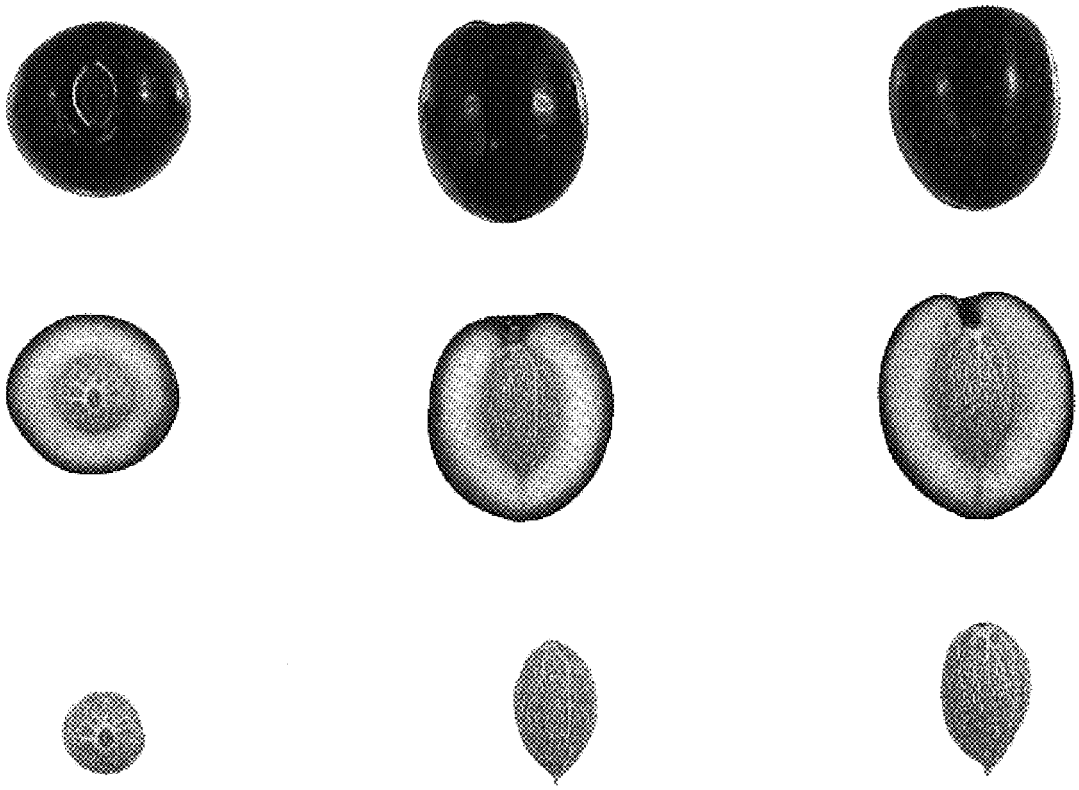
FIG. 3 illustrates typical external (top), internal (middle) views of the fruit and the endocarp (bottom) of the new cultivar.

*Curvature.*—Longitudinally the leaf blade is relatively flat as illustrated in FIG. 2.

*Base.*—Generally cuneate.

*Apex.*—Obtuse.

*Margin.*—Entire.

*Color.*—Commonly Green Group 137A on the upper surface, and Yellow-Green Group 148C on the under surface.

*Central vein.*—Commonly Green Group 139D on the upper surface, and Green Group 141C on the under surface.

Flowers:

*Time.*—Commonly approximately May 1st to May 10th at Córdoba, Spain.

*Flower description.*—Small in size, the corolla consists of 4 petals, there are 2 white stamens which are short and bear relatively large anthers which abundantly produce pollen, and the pistil consisting of an ovary, short style and a bilobed and papillose sigma is located at the center.

*Petal color.*—Near White Group 155C.

Fruit:

*Harvest time.*—Early, commonly approximately 10 days earlier than the 'Arbequina' cultivar at Córdoba, Spain; commonly begins at approximately October 13th and ends at approximately December 6th at Córdoba, Spain for a duration of approximately 53 days which can be compared for a duration of 71 days for the 'Arbequina' cultivar. Accordingly, the harvest duration can be optimized over a shorter time period when growing the new cultivar.

*Shape.*—ovoid and generally symmetrical.

*Maximum transverse diameter.*—Centrally positioned.

*Base.*—Rounded and depressed.

*Apex.*—Rounded.

*Nipple.*—Absent.

*Weight.*—Medium, commonly approximately 2.7±0.1 grams on average which can be compared to approximately 1.8±0.0 grams on average for the 'Arbequina' cultivar under the same growing conditions.

*Fruit yield/canopy volume* ($m^3$).—During the 3rd year approximately 2.9±0.5 kg on average which can be compared to 2.1±0.3 kg on average for the 'Arbequina' cultivar; during the fourth year approximately 6.1±0.7 kg on average which can be compared to 5.5±0.3 kg on average for the 'Arbequina' cultivar; and during the 5th year approximately 5.8±0.6 kg on average which can be compared to 6.0±0.4 kg on average for the 'Arbequina' cultivar.

*Oil yield/canopy volume* ($m^3$).—During the 3rd year approximately 0.5 kg on average which can be compared to 0.3±0.1 kg on average for the 'Arbequina' cultivar; during the 4th year approximately 1.3±0.1 kg on average for both cultivars; and during the 5th year approximately 1.2±0.1 kg on average which can be compared to 1.3±0.1 kg on average for the 'Arbequina' cultivar.

*Removal force.*—Approximately 238.3±7.1 grams on average which can be compared to approximately 210.1±6.7 grams on average for the 'Arbequina' cultivar.

*Weight/removal force.*—Approximately 94.9±4.1 grams on average which can be compared to approximately 132.1±6.3 grams on average for the 'Arbequina' cultivar.

*Oil content* (*fresh fruit*).—Approximately 19.1±0.4% on average which can be compared to approximately 19.4±0.5 weight % on average for the 'Arbequina' cultivar.

*Oil content* (*dry fruit*).—Approximately 48.4±0.5 weight % on average which can be compared to approximately 44.7±0.6 weight % on average for the 'Arbequina' cultivar.

*Moisture content.*—Approximately 60.8±0.7 weight % on average which can be compared to approximately 57.1±0.8 weight % on average for the 'Arbequina' cultivar.

*Color.*—The outer skin is Green Group 141C when immature, and near black, Black Group 202A, when mature, and the fruit flesh is Yellow-White Group 158C when mature.

Endocarp:

*Configuration.*—Elliptic and generally symmetrical.

*Size.*—Commonly approximately 20 mm in length on average, and approximately 8.5 mm in width on average at the widest point.

*Weight.*—Medium.

*Maximum transverse diameter.*—Centrally positioned.

*Base.*—Rounded.

*Apex.*—Sharply pointed (mucro).

*Surface.*—Rugose.

*Number of grooves.*—Medium.

*Color.*—Grey-Brown Group 199C when mature.

During observations to date the new 'Chiquitita' cultivar has displayed no tendency for biennial bearing. Some susceptibility to *Spilocaea oleagina* (Cast.) Hughes and *Colletotrichum* spp. similar to the 'Arbequina' cultivar has been observed.

The fatty acid composition (%) of the oil of the 'Chiquitita' cultivar has been observed to be similar to that of the 'Arbequina' cultivar as reported hereafter wherein mean values are presented.

| | C16:0 Palmitic | C16:1 Palmitoleic | C18:0 Stearic | C18:1 Oleic | C18:2 Linoleic |
|---|---|---|---|---|---|
| 'Chiquitita' | 16.6 + 0.5 | 2.6 + 0.1 | 1.5 + 0.1 | 65.0 + 1.1 | 12.1 + 0.6 |
| 'Arbequina' | 16.5 + 0.5 | 3.1 + 0.1 | 1.6 + 0.1 | 64.4 + 1.3 | 12.1 + 0.8 |

The new 'Chiquitita' cultivar has not been observed under all possible environmental conditions to date. Accordingly, it is possible that the phenotypic expression may vary somewhat with changes in light intensity and duration, cultural practices, and other environmental conditions.

We claim:

1. A new distinct *Olea europaea* tree characterized by the following combination of characteristics:

(a) displays low vigor and a compact and weeping growth habit that is adapted for growing in high density orchards, (b) displays an ability to form an olive crop at an early age, and (c) efficiently forms attractive olives having a high oil content;

substantially as herein shown and described.

* * * * *